United States Patent [19]

Takashima et al.

[11] 4,017,621
[45] Apr. 12, 1977

[54] 2-MORPHOLINYL TRICYCLIC DIBENZAZEPINE COMPOUNDS

[75] Inventors: Yoshinori Takashima, Nishinomiya; Isamu Maruyama, Minoo; Junki Katsube, Toyonaka, all of Japan

[73] Assignee: Sumitomo Chemical Company, Limited, Japan

[22] Filed: Nov. 26, 1975

[21] Appl. No.: 635,355

[30] Foreign Application Priority Data

Dec. 9, 1974 Japan .............................. 49-141691
Dec. 27, 1974 Japan ................................. 50-2911
Apr. 23, 1975 Japan ................................. 50-49891

[52] U.S. Cl. ........................ 424/248.4; 260/239 D; 260/247.1 E; 260/247.2 R; 260/247.5 H; 424/248.58; 424/248.57
[51] Int. Cl.² ....................................... C07D 413/06
[58] Field of Search ............. 260/247.5 H, 247.1 E, 260/247.2 R; 424/248

[56] References Cited
UNITED STATES PATENTS

| | | | |
|---|---|---|---|
| 2,976,281 | 3/1961 | Schindler ..................... | 260/247.5 H |
| 3,467,650 | 9/1969 | Schindler et al. .......... | 260/247.5 H |
| 3,679,662 | 7/1972 | Morita et al. ............... | 260/247.5 H |

*Primary Examiner*—Henry R. Jiles
*Assistant Examiner*—R. W. Ramsuer
*Attorney, Agent, or Firm*—Birch, Stewart, Kolasch and Birch

[57] ABSTRACT

Novel tricyclic compounds of the formula:

wherein A is —$CH_2$—$CH_2$—, —CH=CH— or

—CH——CH—,
    \ /
    $CH_2$

X is hydrogen, halogen, nitro, trifluoromethyl, $C_1$-$C_3$ alkyl or $C_1$-$C_3$ alkoxy, $R_1$ and $R_2$ are each hydrogen or $C_1$-$C_4$ alkyl and $R_3$ is hydrogen, $C_1$-$C_4$ alkyl, $C_3$-$C_5$ alkenyl, $C_3$-$C_5$ alkynyl, $C_3$-$C_6$ cycloalkyl ($C_1$-$C_3$)alkyl, ar($C_1$-$C_3$)alkyl, polyhalo($C_1$-$C_2$)alkyl, $C_1$-$C_4$ alkoxy($C_1$-$C_3$)alkyl or hydroxy($C_1$-$C_3$)alkyl, and non-toxic salts thereof which are useful as antidepressants and can be prepared by reduction of a compound of the formula:

wherein A, X, $R_1$, $R_2$ and $R_3$ are each as defined above.

9 Claims, No Drawings

22-MORPHOLINYL TRICYCLIC DIBENZAZEPINE COMPOUNDS

The present invention relates to novel tricyclic compounds and their production and use. More particularly, it relates to novel tricyclic dibenzazepine derivatives and their non-toxic, pharmaceutically acceptable salts useful as antidepressants and their production and use.

The tricyclic dibenzazepine derivatives provided according to this invention are representable by the formula:

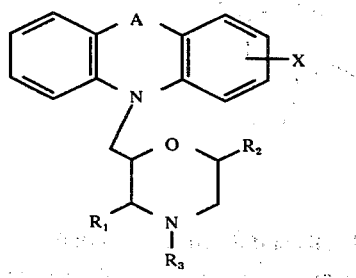

[I]

wherein A is $-CH_2-CH_2-$, $-CH=CH-$ or

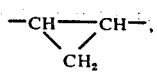

X is hydrogen, halogen, nitro, trifluoromethyl, $C_1-C_3$ alkyl or $C_1-C_3$ alkoxy, $R_1$ and $R_2$, which may be the same or different, are hydrogen or $C_1-C_4$ alkyl and $R_3$ is hydrogen, $C_1-C_4$ alkyl, $C_3-C_5$ alkenyl, $C_3-C_5$ alkynyl, $C_3-C_6$ cycloalkyl$(C_1-C_3)$alkyl, ar$(C_1-C_3)$alkyl, polyhalo$(C_1-C_2)$alkyl, $C_1-C_4$ alkoxy$(C_1-C_3)$alkyl or hydroxy$(C_1-C_3)$alkyl, and their non-toxic, pharmaceutically acceptable salts.

The tricyclic dibenzazepine derivatives [I] and their non-toxic, pharmaceutically acceptable salts have been found to exert various excellent pharmacological properties as antidepressants with low toxicity and are therefore useful as antidepressants.

Thus, the present invention provides the tricyclic dibenzazepine derivatives [I] and non-toxic, pharmaceutically acceptable salts thereof. It also provides a pharmaceutical composition containing a therapeutically effective amount of at least one of the tricyclic dibenzazepine derivatives [I] and non-toxic, pharmaceutically acceptable salts thereof. If further provides a process for producing the tricyclic dibenzazepine derivatives [I] and non-toxic, pharmaceutically acceptable salts thereof.

As used herein, the terms "$C_1-C_3$ alkyl" and "$C_1-C_4$ alkyl" mean straight or branched alkyl having the respective number of carbon atoms (e.g. methyl, ethyl, n-propyl, isopropyl, n-butyl, sec.-butyl). The term "$C_1-C_3$ alkoxy" means straight or branched alkoxy having one to three carbon atoms (i.e. methoxy, ethoxy, n-propoxy, isopropoxy). Examples of "$C_3-C_5$ alkenyl" are propenyl, butenyl, 3,3-dimethylallyl, etc., and examples of "$C_3-C_5$ alkynyl" are propargyl, butynyl, etc. Examples of "$C_3-C_6$ cycloalkyl$(C_1-C_3)$alkyl" are cyclopropylmethyl, cyclopropylethyl, etc., examples of "ar$(C_1-C_3)$alkyl" are benzyl, phenethyl, naphthylmethyl, etc., and examples of "polyhalo$(C_1-C_2)$alkyl" are trifluoromethyl, trifluoroethyl, difluoroethyl, etc. Examples of "$C_1-C_4$ alkoxy$(C_1-C_3)$alkyl" are methoxyethyl, methoxypropyl, ethoxyethyl, ethoxypropyl, n-propoxyethyl, n-propoxypropyl, isopropoxyethyl, isopropoxypropyl, etc., and examples of "hydroxy$(C_1-C_3)$alkyl" are hydroxyethyl, hydroxypropyl, etc. Examples of "halogen" are chlorine, bromine, fluorine, etc.

Examples of non-toxic, pharmaceutically acceptable salts of the tricyclic dibenzazepine derivatives [I] include acid-addition salts such as hydrochloride, hydrobromide, sulfate, acetate, oxalate, citrate, tartrate, succinate, fumarate and lactate.

According to the present invention, the tricyclic dibenzazepine derivatives [I] can be prepared by various methods of which typical examples are as follows:

Method (a)

The tricyclic dibenzazepine derivative [I] can be prepared by reduction of a compound of the formula:

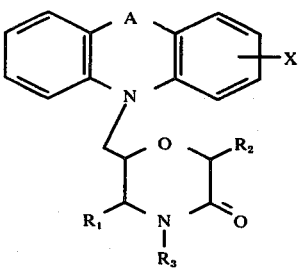

[II]

wherein A, X, $R_1$, $R_2$ and $R_3$ are each as defined above. The reduction may be accomplished by the use of a reducing agent which is conventionally employed in reduction of a lactam

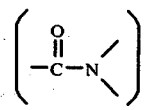

to an amine

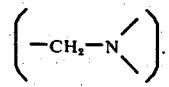

One of the most preferred reducing agents is a metal hydride such as lithium aluminium hydride, sodium bis(2-methoxyethoxy)aluminium hydride or sodium dihydrodiethyl aluminate. The reducing agent can be used in a stoichiometric amount or more to the compound [II]. The temperature for the reduction can be varied from room temperature to the refluxing temperature of the reduction system. The reduction may be carried out optionally in the presence of an inert organic solvent such as ether (e.g. diethyl ether, tetrahydrofuran, dioxane, ethyleneglycol dimethyl ether), an aliphatic hydrocarbon (e.g. heptane, n-hexane, cyclohexane) or an aromtic hydrocarbon (e.g. benzene, toluene). When sodium borohydride is employed as the reducing agent, the presence of a salt such as aluminium chloride is favored.

Method (b)

The tricyclic dibenzazepine derivative of the formula:

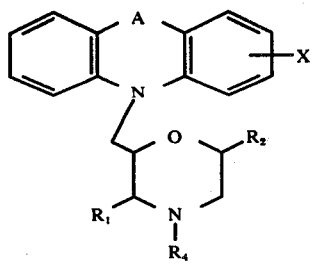

[IA]

wherein A, X, $R_1$ and $R_2$ are each as defined above and $R_4$ is $C_1$-$C_4$ alkyl, $C_3$-$C_5$ alkenyl, $C_3$-$C_5$ alkynyl, $C_3$-$C_6$ cycloalkyl($C_1$-$C_3$)alkyl, ar($C_1$-$C_3$)alkyl, polyhalo($C_1$-$C_2$)alkyl, $C_1$-$C_4$ alkoxy($C_1$-$C_3$)alkyl can be prepared by reacting a compound of the formula:

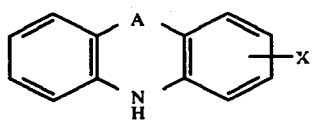

[III]

wherein A and X are each as defined above with a morpholinylmethyl compound of the general formula:

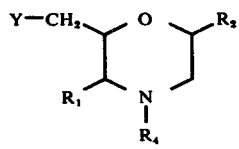

[IV]

wherein $R_1$, $R_2$ and $R_4$ are each as defined above and Y is a conventional leaving group such as halogen (e.g. chlorine, bromine) or sulfonyloxy (e.g. methanesulfonyloxy, p-toluenesulfonyloxy) in an inert organic solvent such as an aromatic hydrocarbon (e.g. benzene, toluene, xylene), dimethylformamide or dimethylsulfoxide in the presence of a base. Examples of the base are metal amides (e.g. sodium amide, potassium amide), metallic sodium, butyl lithium, sodium hydride, etc. The temperature for the reaction can be varied from room temperature to the refluxing temperature of the reaction system.

Method (c)

The tricyclic dibenzazepine derivative of the formula:

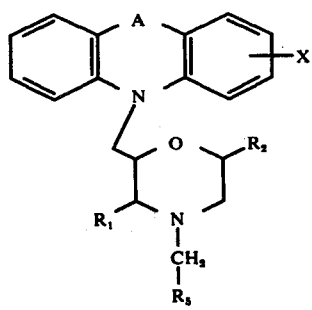

[IB]

wherein A, X, $R_1$ and $R_2$ are each as defined above and $R_5$ is hydrogen, $C_1$-$C_3$ alkyl, $C_3$-$C_4$ alkenyl, $C_3$-$C_4$ alkynyl, $C_3$-$C_6$ cycloalkyl, $C_3$-$C_6$ cycloalkyl($C_1$-$C_6$)alkyl, ar($C_1$-$C_2$) alkyl, polyhalomethyl, $C_1$-$C_4$ alkoxy($C_1$-$C_2$)alkyl, hydroxy($C_1$-$C_2$)alkyl, can be prepared by reducing a compound of the formula:

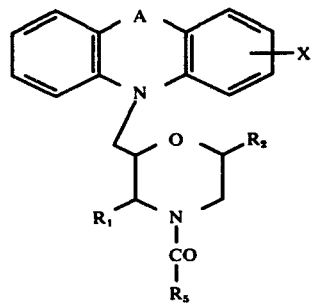

[V]

wherein A, X, $R_1$, $R_2$ and $R_5$ are each as defined above. The reduction may be carried out in the substantially same manner as in Method (a).

Method (d)

The tricyclic dibenzazepine derivative of the formula:

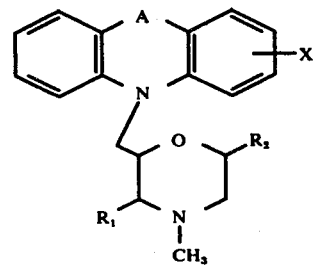

[IC]

wherein A, X, $R_1$ and $R_2$ are each as defined above can be prepared by reducing a compound of the formula:

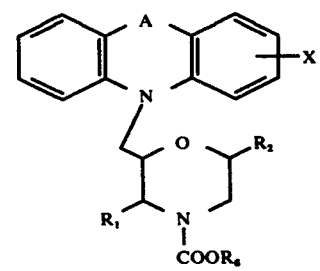

[VI]

wherein A, X, $R_1$ and $R_2$ are each as defined above and $R_6$ is $C_1$-$C_4$ alkyl or aryl. The reduction may be effected in the substantially same manner as in Method (a).

Method (e)

I. The tricyclic dibenzazepine derivative of the formula:

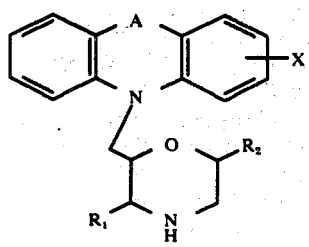

[ID]

wherein A, X, $R_1$ and $R_2$ are each as defined above can be prepared from a compound of the formula:

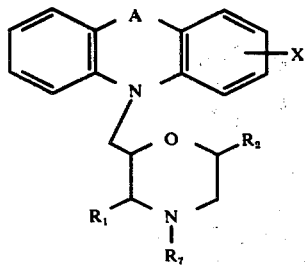

[VII]

wherein A, X, $R_1$ and $R_2$ are each as defined above and $R_7$ is $C_1$-$C_3$ alkyl, ar($C_1$-$C_3$)alkyl by substitution of $R_7$ with hydrogen. One of the most useful procedures for the substitution is the reaction with alkyl or aryl chloroformate (e.g. methyl chloroformate, ethyl chloroformate, phenyl chloroformate), followed by hydrolysis of the resulting alkoxycarbonyl or alkyloxycarbonyl compound. The reaction with the alkyl or aryl chloroformate may be performed at a temperature of from room temperature to the refluxing temperature in an inert organic solvent (e.g. benzene, toluene). The hydrolysis of the resulting alkoxycarbonyl or aryloxycarbonyl compound is carried out in an inert organic solvent (e.g. water, hyrous methanol, hyrous ethanol) in the presence of a base such as a metal hyroxide (e.g. sodium hydroxide, potassium hydroxide) at a temperature of from room temperature to the refluxing temperature.

II. Another useful method for producing the compound of the formula [ID] wherein A is —$CH_2$—$CH_2$— or

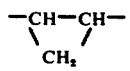

and $R_7$ is benzyl is catalytic hydrogenation. The catalytic hydrogenation may be carried out in the presence of a catalyst such as palladium-on-charcoal (Pd-C) under an atmosphere of hydrogen gas in an inert organic solvent such as an alcohol (e.g. methanol, ethanol). The hydrogen pressure can be 1 atmospheric pressure or higher, and the temperature may be room temperature or higher. The presence of an acid (e.g. hydrochloric acid, acetic acid) in the reduction system may promote the progress of the reaction.

Method (f)

The tricyclic dibenzazepine derivative of the formula:

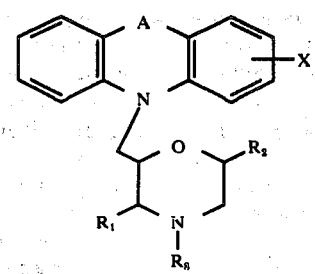

[IE]

wherein A, X, $R_1$ and $R_2$ are each as defined above and $R_8$ is $C_1$-$C_4$ alkyl, $C_3$-$C_5$ alkenyl, $C_3$-$C_5$ alkynyl, $C_3$-$C_6$ cycloalkyl-($C_1$-$C_3$)alkyl, ar($C_1$-$C_3$)alkyl, polyhalo($C_1$-$C_2$)alkyl, $C_1$-$C_4$ alkoxy($C_1$-$C_3$)alkyl or hydroxy($C_1$-$C_3$)alkyl can be prepared by condensation of the compound [ID] with a compound of the formula:

$$Z-R_8 \qquad [VIII]$$

wherein $R_8$ is as defined above and Z is a conventional leaving group such as halogen (e.g. chlorine, bromine) or sulfonyloxy (e.g. methanesulfonyloxy, p-toluenesulfonyloxy, trichloromethylsulfonyloxy) in an inert organic solvent such as an aromatic hydrocarbon (e.g. benzene, toluene, xylene), dimethylformamide, dimethylsulfoxide or an alcohol (e.g. methanol, ethanol, propanol) in the presence of a base. Examples of the base are metal carbonate (e.g. sodium carbonate, potassium carbonate), metal bicarbonate (e.g. sodium bicarbonate, potassium bicarbonate), metal hydroxide (e.g. sodium hydroxide, potassium hydroxide, metal hydride (e.g. sodium hydride, potassium hydride), lower alkalamine (e.g. triethylamine) or metal alkoxide (e.g. sodium methoxide, sodium ethoxide). The base may be used in a stoichiometric amount or more. The temperature for the condensation can be varied from room temperature to the refluxing temperature of the reaction system.

Method (g)

The tricyclic dibenzazepine derivative [IE] wherein $R_8$ is —$CH_2$—$R_9$ can be prepared by condensation-reduction of the corresponding compound [ID] with a carbonyl compound of the formula:

[IX]

wherein $R_9$ is hydrogen, $C_1$-$C_3$ alkyl, $C_3$-$C_4$ alkenyl, $C_3$-$C_4$ alkynyl, $C_3$-$C_6$ cycloalkyl($C_1$-$C_2$)alkyl, ar($C_1$-$C_2$)alkyl, polyhalomethyl, $C_1$-$C_4$ alkoxy($C_1$-$C_2$)alkyl or hydroxy($C_1$-$C_2$)-alkyl.

The condensation-reduction can be accomplished by several per se known procedures. The usual procedure of Leuckart-Wallach reaction using formic acid is applicable to the condensation-reduction [Organic Reactions, Vol. 5, p. 301, John Wiley & Sons, Inc.]. For instance, the corresponding compound [IX] is added to a mixture of amineformate of the compound [ID] and formic acid, and the resultant mixture is heated at a temperature from room temperature to 200° C.

The condensation-reduction can be also accomplished by hydrogenation of a mixture of the compound [ID] and the compound [IX] over a catalyst such as Raney nickel, platinum oxide or palladium in the presence or absence of an inert organic solvent. The pressure may be 1 atmospheric pressure or higher. A condensation agent such as sodium acetate may be used.

The condensation-reduction can be further accomplished by using the sodium-alcohol or zinc-acid or alkali method. Examples of an inert organic solvent are alcohols (e.g. methanol, ethanol, isopropanol), liquid ammonia, acetic acid and ethers (e.g. diethyl ether, diisopropyl ether, tetrahydrofuran, dioxane).

Moreover, the condensation-reduction can be accomplished by the reduction of the Schiff base or enamine prepared from the compound [ID] and the compound [IX] in a conventional procedure. The reduction may be performed in the same manner as the hydrogenation procedure described above. A reducing agent such as sodium borohydride, diborane, lithium aluminium hydride, sodium aluminium diethyldihydride, sodium borocyano hydride and bis(2-methoxyethoxy)aluminium hydride can be used in the reduction in an inert solvent such as an alcohol (e.g. methanol, ethanol, isopropanol, n-butanol, t-butanol), an aromatic hydrocarbon (e.g. benzene, toluene) or an ether (e.g. diethyl ether, diisopropyl ether, dioxane, tetrahydrofuran). The temperature for the treatment in this case can be varied from $-10°$ C to the refluxing temperature of the reduction system.

Method (h)

The tricyclic dibenzazepine derivative of the formula:

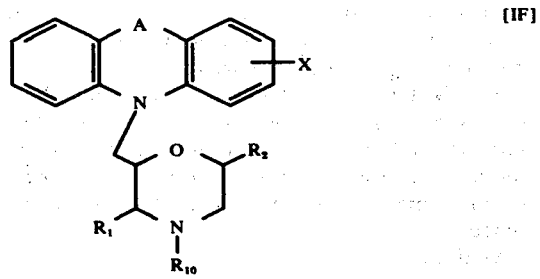

[IF]

wherein A, X, $R_1$ and $R_2$ are each as defined above and $R_{10}$ is hydrogen, $C_1$-$C_4$ alkyl, $C_3$-$C_5$ alkenyl, $C_3$-$C_5$ alkynyl, $C_3$-$C_6$ cycloalkyl($C_1$-$C_3$)alkyl, ar($C_1$-$C_3$) alkyl, polyhalo($C1$-$C_2$)-alkyl, $C_1$-$C_4$ alkoxy($C_1$-$C_3$)alkyl can be prepared by reacting the corresponding epoxide of the formula:

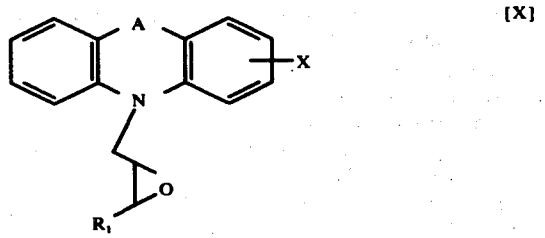

[X]

wherein A, X and $R_1$ are each as defined above with an ethylamine derivative of the formula:

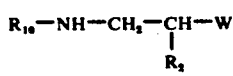

[XI]

wherein $R_2$ and $R_{10}$ are each as defined above and W is a conventional leaving group such as halogen (e.g. chlorine, bromine) or sulfonyloxy [e.g. $-OSO_2R_{12}$ (wherein $R_{12}$ is hydroxy, $C_1$-$C_3$ alkyl, aryl, $C_1$-$C_3$ alkoxy, aryloxy)] in an inert solvent such as an alcohol (e.g. methanol, ethanol, isopropanol, ethyleneglycol), an ether (e.g. diethyl ether, tetrahydrofuran, dioxane), an aromatic hydrocarbon (e.g. benzene, toluene) or their mixture in the presence of a base such as a metal hydroxide (e.g sodium hydroxide, potassium hydroxide, barium hydroxide), followed by treatment of the intermediary product with a base.

The first step of this reaction is the amination of the epoxide [X] with the ethylamine derivative [IX] to give the aminoalcohol of the formula:

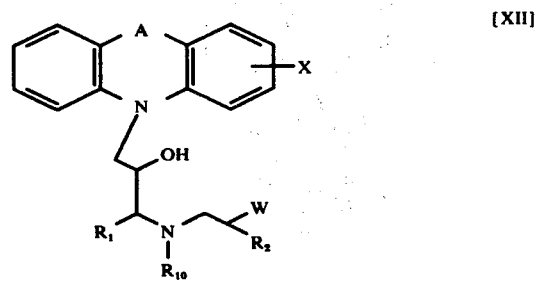

[XII]

wherein A, X, $R_1$, $R_2$ and $R_{10}$ are each as defined above. The second step is the condensation of the resulting aminoalcohol [XII] in the presence of a base. The tricyclic dibenzazepine derivative [IF] can be produced without separation of the intermediary aminoalcohol [XII]. The temperature for the treatment can be varied from room temperature to the refluxing temperature of the reaction system. The basic binding agent may be used in a stoichiometric amount or more.

Method (i)

The tricyclic dibenzazepine derivative [IF] can be prepared by intramolecular dehydration of the corresponding dialcohol of the formula:

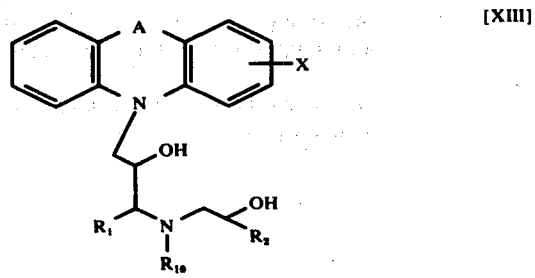

[XIII]

wherein A, X, $R_1$, $R_2$ and $R_{10}$ are each as defined above in the presence of an acid (e.g. sulfuric acid, hydrochloric acid, p-toluenesulfonic acid, polyphosphoric acid, thionyl chloride in the presence or absence of an inert solvent (e.g. benzene, toluene, xylene). The reaction temperature can be varied from room temperature to the refluxing temperature of the reaction system.

The thus obtained tricyclic dibenzazepine derivatives [I]can be converted into their salts by a conventional procedure, and reconversion from the salts to the original free bases can be also carried out in a conventional manner.

As stated previously, the tricyclic dibenzazepine derivatives [I] and their non-toxic pharmaceutically acceptable salts are useful as excellent antidepressants. They exhibit various pharmacological activities, especially on central nervous system and auto-nervous system. For instance, they have been found to antagonize the central nervous system depressant effect induced by tetrabenazine and reserpine and the choline effect in the central nervous system induced by tremorine and potentiate the methamphetamine effect and the central and peripheral action of norepinephirine. Furthermore, their acute cardio-toxicity is significantly lower compared with that of known standard antidepressants. The acute toxicity of these compounds is relatively low or mild compared to that of known standard antidepressants.

In view of their pharmacological properties, the preferred tricyclic dibenzazepine derivatives [I] are those wherein $R_1$ and $R_2$ are each hydrogen, $R_3$ is hyrogen, $C_1$-$C_3$ alkyl, cyclopropylmethyl, dimethylallyl or $C_1$-$C_3$ alkoxy($C_1$-$C_3$)alkyl and X is hydrogen or chlorine, and acid-addition salts thereof.

More preferred are those wherein X, $R_1$ and $R_2$ are each hydrogen and $R_3$ is hydrogen or $C_1$-$C_3$ alkyl (preferably methyl) and acid-addition salts thereof.

The most preferred are those wherein X, $R_1$ and $R_2$ are each hydrogen, $R_3$ is hydrogen or $C_1$-$C_3$ alkyl (preferably methyl) and A is —CH=CH—, and acid-addition salts thereof.

In treating mental depression, the tricyclic dibenzazepine derivatives [I] and their non-toxic pharmaceutically acceptable acid-addition salts may be are administered orally or parenterally at a daily dose of 5 to 300 mg/adult person (60 kg of body weight) in a conventional dosage unit form.

For the oral or parenteral administration, they are made up alone or together with a conventional pharmaceutical carrier or diluent to a conventional solid or liquid pharmaceutical preparation (e.g. powders, granules, tablets, capsules, suspensions, emulsions, solutions) using the conventional methods in pharmacuetical field.

The intermediate tricyclic dibenzazepine compounds [II], for example, can conventionally be prepared from the tricyclic dibenzazepine compounds of the general formula:

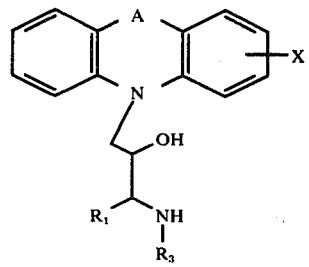

[XIV]

wherein A, X, $R_1$ and $R_3$ are each as defined above according to the following steps:

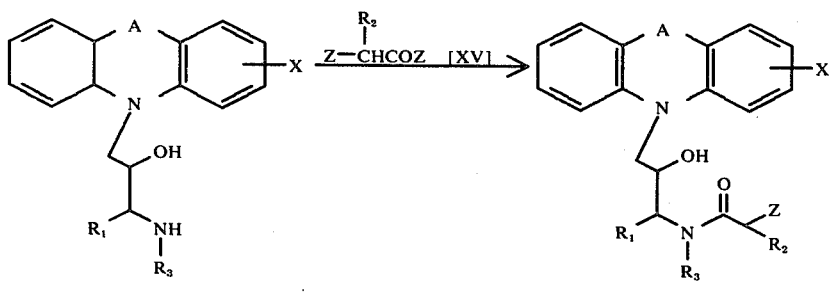

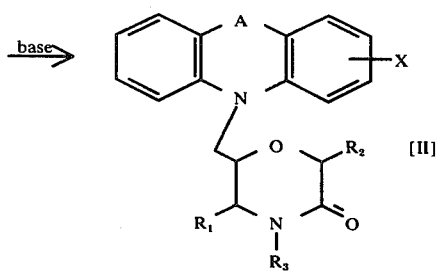

wherein A, X, $R_1$, $R_2$, $R_3$ and Z are each as defined above.

The first step is the acylation of the tricyclic dibenzazepine compound [II] with the acyl compound [XV] in the presence or absence of a base in an inert solvent. The second step is the cyclization of the tricyclic dibenzazepine compound [XVI] with a base in an inert solvent.

The intermediate tricyclic dibenzazepine compound [V], for example, can conventionally be prepared by acylation of the tricyclic dibenzazepine compound [ID], e.g. treatment of the latter withh an acylating agent in the presence or absence of a base in an inert solvent.

The following examples are given to illustrate the present invention more precisely.

EXAMPLE 1

To a suspension of lithium aluminum hydride (0.03 g) in tetrahydrofuran (5 ml) was added a solution of 5-(4-benzyl-5-oxo-2-morpholinylmethyl)-10,11-dihydro-5H-dibenz-[b,f]azepine (0.5 g) in tetrahydrofuran (15 ml) under ice cooling, and the resulting mixture was stirred at room temperature for 1 hour and refluxed for 10 hours with stirring. The reaction mixture was cooled, admixed with water (2 ml) and extracted with benzene. The benzene extract was washed with water, dried over anhydrous sodium sulfate and evaporated to afford 5-(4-benzyl-2-morpholinylmethyl)-10,11-dihydro-5H-dibenz[b,f]azepine as an oily substance. M.P. 139°–140° C (oxalate).

The starting 5-(4-benzyl-5-oxo-2-morpholinylmethyl)-10,11-dihydro-5H-dibenz[b,f]azepine was prepared as follows:

To a solution of crude 5-(2-hydroxy-3-benzylaminopropyl)-10,11-dihydro-5H-dibenz[b,f]azepine (2.8 g) in methylene chloride (40 were was added 10% aqueous sodium hydroxide (3.5 g) and chloroacetyl chloride (1 g) under ice cooling. After stirring for 2 hours, water was added to the reaction mixture. The organic layer was separated, washed with water, dried and evaporated to afford 5-[2-hydroxy-3-(N-chloroacetyl)-benzylaminopropyl]-10,11-dihydro-5H-dibenz-[b,f]azepine as an oily substance (3.1 g). A solution of this oil in methanol (50 ml) was added to a solution of metallic sodium (0.18 g) in methanol (10 ml), and the mixture was stirred under reflux for 20 hours. The solvent was removed by evaporation under reduced pressure, and the residue was partitioned between water and chloroform. The chloroform layer was washed, dried and evaporated to afford 5-(4-benzyl-5-oxo-2-morpholinylmethyl)-10,11-dihydro-5H-dibenz[b,f]azepine as an oily substance (3.6 g).

In the same procedure as above, the following compounds are obtained:

5-(4-Benzyl-5-oxo-2-morpholinylmethyl)-5H-dibenz[b,f]azepine;

6-(4-Benzyl-5-oxo-2-morpholinylmethyl)-1,1a,6,10b-tetrahydrodibenz[b,f]cyclopropa[d]azepine.

EXAMPLE 2

To a suspension of sodium amide (0.5 g) in benzene was added a solution of 10,11-dihydro-5H-dibenz[b,f]azepine (1.0 g) in benzene at room temperature, and the resulting mixture was stirred under reflux for 1 hour. After cooling, a solution of 4-isopropyl-2-chloromethylmorpholine (1.0 g) in benzene was added to the reaction mixture at room temperature, and the resulting mixture was stirred at room temperature for 1 hour and refluxed for 20 hours with stirring. The reaction mixture was cooled and admixed with water. The benzene layer was separated, washed with water, dried over anhydrous magnesium sulfate and evaporated to afford 5-(4-isopropyl-2-morpholinylmethyl)-10,11-dihydro-5H-dibenz[b,f]azepine as an oily substance. M.P. 203.5° — 204.5° C (oxalate).

EXAMPLE 3

To a suspension of lithium aluminium hydride (0.08 g) in tetrahydrofuran was added a solution of 5-(4-acetyl-2-morpholinylmethyl)-10,11-dihydro-5H-dibenz[b,f]azepine (0.34 g) in tetrahydrofuran under ice-cooling, and the resulting mixture was stirred under reflux for 1 hour. the reaction mixture was cooled, admixed with water and extracted with benzene. The benzene extract was washed with water, dried over anhydrous sodium sulfate and evaporated to afford 5-(4-ethyl-2-morpholinylmethyl)-10,11-dihydro-5H-dibenz[b,f]azepine as an oily substance. M.P. 210°–211° C (oxalate).

The starting 5-(4-acetyl-2-morpholinylmethyl)-10,11-dihydro-5H-dibenz[b,f]azepine was prepared as follows:

To a solution of 5-(2-morpholinylmethyl)-10,11-dihydro-5H-dibenz[b,f]azepine (0.34 g) in anhydrous benzene was added excess acetyl chloride under ice cooling. After stirring for 4 hours, the reaction mixture was washed with aqueous 2N sodium hydroxide and then with water, dried and evaporated to afford 5-(4-acetyl-2-morpholinylmethyl)-10,11-dihydro-5H-dibenz[b,f]azepine as an oily substance.

In the same procedure as above, the following compounds are obtained:

5-(4-Acetyl-2-morpholinylmethyl)-5H-dibenz[b,f]azepine;

6-(4-Acetyl-2-morpholinylmethyl)-1,1a,6,10b-tetrahydrodibenz[b,f]cyclopropa[d]azepine.

EXAMPLE 4

In the same manner as in Example 3, 5-(4-methyl-2-morpholinylmethyl)-10,11-dihydro-5H-dibenz[b,f]azepine was obtained as an oily substance from 5-(4-ethoxycarbonyl-2-morpholinylmethyl)-10,11-dihydro-5H-dibenz[b,f]azepine. M.P. 210°–211° C (oxalate).

EXAMPLE 5

A mixture of 5-(4-benzyl-2-morpholinylmethyl)-10,11-dihydro-5H-dibenz[b,f]azepine (1.62 g) and ethyl chloroformate (1.44 g) in benzene was stirred under reflux for 8 hours. The reaction mixture was cooled, admixed with 10% aqueous sodium hydroxide and extracted with benzene. The benzene extract was dried over anhydrous sodium sulfate and evaporated to afford 5-(4-ethoxycarbonyl-2-morpholinylmethyl)-10,11-dihydro-5H-dibenz[b,f]azepine as an oily substance. To a solution of the oil in ethanol was added 30% aqueous sodium hydroxide, and the resulting mixture was stirred at 65° C for 5 hours. The reaction mixture was cooled and extracted with benzene. The benzene extract was dried over anhydrous sodium sulfate and evaporated to afford 5-(2-morpholinylmethyl)-10,11-dihydro-5H-dibenz[b,f]azepine as an oily substance. M.P. 194.5°–195.5° C (oxalate).

EXAMPLE 6

3-Ethyl-5-(4-benzyl-2-morpholinylmethyl)-10,11-dihydro-5H-dibenz[b,f]azepine (0.6 g) in ethanol and conc. hydrochloric acid (1 ml) was hydrogenated over 10% palladium-on-charcoal (0.4 g) . The reaction mixture was filtered, and the filtrate was concentrated to dryness. The residue was dissolved in benzene, washed with 10% aqueous sodium hydroxide and water, dried over anhydrous sodium sulfate and evaporated to afford 3-ethyl-5-(2-morpholinylmethyl)-10,11-dihydro-5H-dibenz[b,f]azepine. M.P. 146°–150° C (oxalate).

EXAMPLE 7

To a suspension of sodium hydride (0.05 g) in dimethylformamide was added a solution of 5-(2-morpholinylmethyl)-5H-dibenz[b,f]azepine (0.2 g) in dimethylformamide under ice cooling, and the resulting mixture was stirred at room temperature for 30 minutes. To the mixture was added a solution of 3,3-dimethylallyl bromide (0.12 g) in dimethylformamide, and the reaction mixture was stirred at room temperature for 3 hours, cooled, admixed with water and extracted with benzene. The benzene extract was washed with water, dried over anhydrous sodium sulfate and evaporated to afford 5- 4-(3,3-dimethylallyl)-2-morpholinylmethyl -5H-dibenz[b,f]azepine. M.P. 99°–100° C.

EXAMPLE 8

A mixture of 5-(2-morpholinylmethyl)-10,11-dihydro-5H-dibenz[b,f]azepine (0.2 g), potassium carbonate (0.1 g) and ethylenebromohydrin (0.1 g) in water and ethanol was stirred under reflux for 10 hours. The reaction mixture was concentrated and extracted with chloroform. The chloroform extract was washed with water, dried over anhydrous sodium sulfate and evaporated to afford 5-(4-hydroxyethyl-2-morpholinylmethyl)-10,11-dihydro-5H-dibenz[b,f]azepine as an oily substance. M.P. 186°–188° C (oxalate).

EXAMPLE 9

To a suspension of sodium amide (0.08 g) in benzene was added a solution of 5-(2-morpholinylmethyl)-10,11-dihydro-5H-dibenz[b,f]azepine (0.5 g) in benzene under ice cooling, and the resulting mixture was stirred at room temperature for 30 minutes. to the reaction mixture was added a solution of ethyl bromide (0.22 g) in benzene under ice cooling, and the resulting mixture was stirred at room temperature for 4 hours. The reaction mixture was cooled, admixed with water and extracted with benzene. The benzene extract was washed with water, dried over anhydrous sodium sulfate and evaporated to afford 5-(4-ethyl-2-morpholinylmethyl)-10,11-dihydro-5H-dibenz[b,f]azepine as an oily substance.

EXAMPLE 10

To a solution of 5-(2-morpholinylmethyl)-5H-dibenz[b,f]azepine (0.23 g) in tetrahydrofuran was added sodium amide (0.063 g). The resulting mixture was stirred at 40° C for 30 minutes. To the reaction mixture was added trifluoroethyl trichloromethylsulfonate (0.265 g) in tetrahydrofuran at room temperature. The resulting mixture was stirred at 50° C for 5 hours. After cooling, the reaction mixture was admixed with water and extracted with ethyl acetate. The ethyl acetate extract was washed with water, dried over anhydrous sodium sulfate and evaporated to afford 5-(4-trifluoroethyl-2-morpholinylmethyl)-5H-dibenz[b,f]azepine. M.P. 97°–98° C.

EXAMPLE 11

A mixture of 3-ethyl-5-(2-morpholinylmethyl)-10,11-dihydro-5H-dibenz[b,f]azepine (0.3 g), 90% formic acid (0.7 g) and 37% formalin (0.58 ml) was stirred at 90°–100° C for 8 hours. After cooling, 4N hydrochloric acid was added to the reaction mixture. The resulting mixture was evaporated to dryness under reduced pressure. Water was added to the residue, neutralized with aqueous ammonia, and extracted with benzene. The benzene extract was washed with water, dried over anhydrous sodium sulfate and evaporated to afford 3-ethyl-5-(4-methyl-2-morpholinylmethyl)-10,11-dihydro-5H-dibenz[b,f]azepine as an oily substance. M.P. 168°–170° C (oxalate).

EXAMPLE 12

A mixture of 5-(2,3-epoxypropyl)-10,11-dihydro-5H-dibenz[b,f9 azepine (1.0 g), 2-aminoethyl hydrogensulfate (3.83 g) and sodium hydroxide (2.46 g) in water (12.6 ml) and ethanol (16.4 ml) was stirred under reflux for 17 hours. The reaction mixture was concentrated and extracted with chloroform. The chloroform extract was washed with water, dried over anhydrous sodium sulfate and evaporated to afford 5-(2-morpholinylmethyl)-10,11-dihydro-5H-dibenz[b,f]azepine as an oily substance.

EXAMPLE 13 a mixture of 5-(N-methyl-N-β-hydroxyethylamino-2-hydroxypropyl)-10,11-dihydro-5H-dibenz[b,f]azepine (0.3 g) and conc. sulfuric acid (1.5 ml) was stirred at 80° C for 5 hours. Water was added to the cooled reaction mixture, neutralized with aqueous ammonia and extracted with benzene. The benzene extract was washed with water, dried over anhydrous sodium sulfate and evaporated to afford 5-(4-methyl-2-morpholinylmethyl9-10,11-dihydro-5H-dibenz[b,f]azepine as an oily substance.

The following compounds are produced by one or more procedures as above:

5-(2-Morpholinylmethyl)-10,11-dihydro-5H-debenz[b,f]azepine, M.P. 194.5°–195.5° C (oxalate);

5-(2-Morpholinylmethyl)-5H-dibenz[b,f]azepine, M.P. 133°–135° C;

6-(2-Morpholinylmethyl)-1,1a,6,10b-tetrahydrodibenz[b,f]cyclopropa[d]azepine, M.P. 223°–225° C (oxalate);

5-(4-Methyl-2-morpholinylmethyl)-10,11-dihydro-5H-dibenz[b,f]azepine, M.P. 210°–211° C (oxalate);

3-Ethyl-5-(4-methyl-2-morpholinylmethyl)-10,11-dihydro-5H-dibenz[b,f]azepine, M.P. 168°–170° C (oxalate);

3-Ethyl-5-(2-morpholinylmethyl)-10,11-dihydro-5H-dibenz[b,f]azepine, M.P. 146°–150° C (oxalate);

5-(4-Methyl-2-morpholinylmethyl)-5H-dibenz[b,f]azepine, M.P. 207°–209° C (oxalate);

6-(4-Methyl-2-morpholinylmethyl)-1,1a,6,10b-tetrahydrodibenz[b,f]cyclopropa[d]azepine, M.P. 224.5°–225.5° C (oxalate);

5-(4-Ethyl-2-morpholinylmethyl)-10,11-dihydro-5H-dibenz[b,f]azepine, M.P. 210°–211° C (oxalate);

5-(4-Ethyl-2-morpholinylmethyl)-5H-dibenz[b,f]azepine, M.P. 99.5°–100.5° C (oxalate);

6-(4-Ethyl-2-morpholinymethyl)-1,1a,6,10b-tetrahydrodibenz[b,f]cyclopropa[d]azepine, M.P. 226°–229° C (oxalate);

5-(4-Isopropyl-2-morpholinylmethyl)-5H-dibenz[b,f]azepine, M.P. 146°–147° C (oxalate);

5-(4-Isopropyl-2-morpholinylmethyl)-10,11-dihydro-5H-dibenz[b,f]azepine, M.P. 203.5°–204.5° C (oxalate);

5-(4-Isobutyl-2-morpholinylmethyl)-10,11-dihydro-5H-dibenz[b,f]azepine, M.P. 137°–138° C (oxalate);

5-[4-(3,3-Dimethylallyl)-2-morpholinylmethyl]-10,11-dihydro-5H-dibenz[b,f]azepine, M.P. 94°–95° C (oxalate);

6-[4-(3,3-Dimethylallyl)-2-morpholinylmethyl]-1,1a,6,10b-tetrahydrodibenz[b,f]cyclopropa[d]azepine, M.P. 177°–180° C (oxalate);

5-(4-Cyclopropylmethyl-2-morpholinylmethyl)-10,11-dihydro-5H-dibenz[b,f]azepine, M.P. 161.5°–162.5° C (oxalate);

5-(4-Cyclopropylmethyl-2-morpholinylmethyl)-5H-dibenz[b,f]azepine, M.P. 153.5°–154.5° C (oxalate);

6-(4-Cyclopropylmethyl-2-morpholinylmethyl)-1,1a,6,10b-tetrahydrodibenz[b,f]cyclopropa[d]azepine, M.P. 206°–207° C (oxalate);

5-(4-Benzuyl-2-morpholinylmethyl)-5H-dibenz[b,f]azepine, M.P. 122°–123° C;

5-(4-Benzyl-2-morpholinylmethyl)-10,11-dihydro-5H-dibenz[b,f]azepine, M.P. 139°-140° C (oxalate);

5-[4-(3,3-Dimethylallyl)-2-morpholinylmethyl]-5H-dibenz[b,f]azepine, M.P. 99°-100° C;

5-[4-(β-Hydroxyethyl)-2-morpholinylmethyl]-10,11-dihydro-5H-dibenz[b,f]azepine, M.P. 186°-188° C (oxalate);

5-(4-Trifluoromethyl-2-morpholinylmethyl)-5H-dibenz[b,f]azepine, M.P. 97°-98° C;

6-(4-Benzyl-2-morpholinylmethyl)-1,1a,6,10b-tetrahydrodibenz[b,f]cyclopropa[d]azepine, M.P. 188.5°-111° C (oxalate);

5-(4-Propargyl-2-morpholinylmethyl)-5H-dibenz[b,f]azepine, M.P. 145°-147° C;

6-(4-Propargyl-2-morpholinylmethyl)-1,1a,6,10b-tetrahydrodibenz[b,f]cyclopropa[d]azepine, infrared absorption spectrum (film): 3380, 3050, 3000, 2950, 2900, 2850, 2825, 1600, 1580, 1490, 1455, 1230, 1110, 1080, 770, 750, 745 cm$^{-1}$;

5-(4-β-Methoxyethyl-2-morpholinylmethyl)-10,11-dihydro-5H-dibenz[b,f]azepine, M.P. 148°-149°πC )oxalate;

5-(4-γ-Methoxypropyl-2-morpholinylmethyl)-10,11-dihydro-5H-dibenz[b,f]azepine, M.P. 128.5°-129.5° C (oxalate);

5-(4γ-Isopropoxypropyl-2-morpholinylmethyl)-10,11-dihydro-5H-dibenz[b,f]azepine, M.P. 133°-135° C (oxalate);

5-(4-γ-Hydroxypropyl-2-morpholinylmethyl)-10,11-dihydro-5H-dibenz[b,f]azepine, infrared absorption spectrum: 330 – 3400, 2900, 2840, 1595, 1485, 1445, 1335, 1110, 1040, 760, 750, 740 cm$^{-1}$;

5-(4-β-Methoxyethyl-6-methyl-2-morpholinylmethyl)-5H-dibenz[b,f]azepine, inrared absorption spectrum: 2950, 2850, 1590, 1480, 1100, 1080, 750 cm$^{-1}$;

5-(4-β-Hydroxyethyl-2-morpholinylmethyl)-5H-dibenz[b,f]azepine, M.P. 169.5°-170.5° C (oxalate);

6-(4-β-HYdroxyethyl-2-morpholinylmethyl)-1,1a,5,10b-tetrahydrodibenz[b,f]cyclorpopa[d]azepine, M.P. 203.5°-206.0° C (oxalate), etc.

Examples of other typical tricyclic dibenzazepine derivatives provided by the invention are as follows:

3-Chloro-5-(2-morpholinylmethyl)-10,11-dihydro-5H-dibenz[b,f]azepine;

3-Chloro-5-(2-morpholinylmethyl)-5H-dibenz[b,f]azepine;

4-Chloro-6-(2-morpholinylmethyl)-1,1a,6,10b-tetrahydrodibenz[b,f]cyclopropa[d]azepine;

3-Chloro-5-(4-methyl-2-morpholinylmethyl)-10,11-dihydro-5H-dibenz[b,f]azepine;

3Chloro5-(4-methyl-2-morpholinylmethyl)-5H-dibenz[b,f]azepine;

4-Chloro-6-(4-methyl-2-morpholinylmethyl)-1,1a,6,10b-tetrahydrodibenz[b,f]cyclopropa[d]azepine;

3-Chloro-5-(4-benzyl-2-morpholinylmethyl)-10,11-dihydro-5H-dibenz[b,f]azepine;

3-Chloro-5-(4-benzyl-2-morpholinylmethyl)-5H-dibenz[b,f]azepine;

4-Chloro-6-(4-benzyl-2-morpholinylmethyl)-1,1a,6,10b-tetrahydrodibenz[b,f]cyclopropa[d]azepine;

3-Nitro-5-(4-isopropyl-2-morpholinylmethyl)-10,11-dihydro-5H-dibenz[b,f]azepine;

3-Nitro-5-(4-isopropyl-2-morpholinylmethyl)-5H-dibenz[b,f]azepine;

3-Trifluoromethyl-5-(2-morpholinylmethyl)-10,11-dihydro-5H-dibenz[b,f]azepine;

3-Trifluoromethyl-5-(2-morpholinylmethyl)-5H-dibenz[b,f]azepine;

4-Trifluoromethyl-6-(2-morpholinylmethyl)-1,1a,6,10b-tetrahydrodibenz[b,f]cyclopropa[d]azepine;

3-Methoxy-5-(2-morpholinylmethyl)-10,11-dihydro-5H-dibenz[b,f]azepine;

3-Methoxy-5-(2-morpholinylmethyl)-5H-dibenz[b,f]azepine;

4-Methoxy-6-(2-morpholinylmethyl)-1,1a,6,10b-tetrahydrodibenz[b,f]cyclopropa[d]azepine;

5-(3-Methyl-2-morpholinylmethyl)-5H-dibenz[b,f]azepine, etc.

What is claimed is:

1. A compound of the formula:

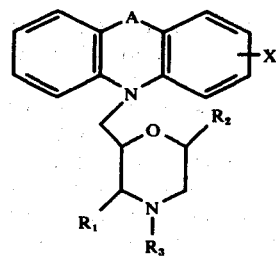

wherein A is —CH$_2$—CH$_2$—, —CH=CH— or

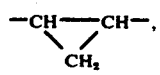

X is hydrogen, halogen, nitro, trifluoromethyl, C$_1$—C$_3$ alkyl or C$_1$—C$_3$ alkoxy, R$_1$ and R$_2$ are each hydrogen or C$_1$—C$_4$ alkyl and R$_3$ is hydrogen, C$_1$—C$_4$ alkyl, C$_3$—C$_5$ alkenyl, C$_3$—C$_5$ alkynyl, C$_3$—C$_6$ cycloalkyl (C$_2$—C$_3$) alkyl, ar(C$_1$—C$_3$) alkyl, polyhalo(C$_1$—C$_2$)alkyl, C$_1$—C$_4$ alkoxy(C$_1$—C$_3$) alkyl or hydroxy(C$_1$—C$_3$)alkyl, or a non-toxic pharmaceutically acceptable salt thereof.

2. A compound according to claim 1, wherein R$_1$ and R$_2$ are each hydrogen, R$_3$ is hydrogen, C$_1$—C$_3$ alkyl, cyclopropylmethyl, dimethylallyl or C$_1$—C$_3$ alkoxy(C$_1$—C$_3$)alkyl and X is hydrogen or chlorine.

3. A compound according to claim 1, wherein R$_1$, R$_2$ and X are each hydrogen and R$_3$ is hydrogen or C$_1$—C$_3$ alkyl.

4. A compound according to claim 3, wherein R$_3$ is hydrogen or methyl.

5. A compound according to claim 4, wherein A is —CH$_2$—CH$_2$—.

6. A compound according to claim 4, wherein A is —CH=CH—.

7. A compound according to claim 4, wherein A is

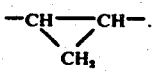

8. An antidepressant composition which comprises an antidepressant effective amount of at least one compound according to claim 1 as an active ingredient and a pharmaceutically acceptable carrier or diluent.

9. A method for treatment of mental depression which comprises administering to a person an antidepressant effective amount of at least one compound according to claim 1.

* * * * *